United States Patent
Dach et al.

(10) Patent No.: US 8,513,413 B2
(45) Date of Patent: Aug. 20, 2013

(54) PROCESS FOR THE PREPARATION OF NITROOROTIC ACID

(75) Inventors: Rolf Dach, Gau-Algesheim (DE); Xiangrui Jiang, Shanghai (CN); Jingshan Shen, Shanghai (CN); Jin Suo, Shanghai (CN); Yi Zhu, Shanghai (CN)

(73) Assignee: Boehringer Ingelheim Pharma GmbH & Co. KG, Ingelheim am Rhein (DE)

( * ) Notice: Subject to any disclaimer, the term of this patent is extended or adjusted under 35 U.S.C. 154(b) by 22 days.

(21) Appl. No.: 13/201,486

(22) PCT Filed: Feb. 22, 2010

(86) PCT No.: PCT/EP2010/052188
§ 371 (c)(1), (2), (4) Date: Oct. 24, 2011

(87) PCT Pub. No.: WO2010/094791
PCT Pub. Date: Aug. 26, 2010

(65) Prior Publication Data
US 2012/0123118 A1    May 17, 2012

(30) Foreign Application Priority Data
Feb. 23, 2009 (CN) .......................... 2009 1 0007568

(51) Int. Cl.
*C07D 239/02* (2006.01)

(52) U.S. Cl.
USPC .......................................................... 544/311

(58) Field of Classification Search
None
See application file for complete search history.

(56) References Cited

FOREIGN PATENT DOCUMENTS
DE    2600542 A1    7/1976

OTHER PUBLICATIONS

International Search Report, Form PCT/ISA/210, and Written Opinion, Form PCT/ISA/237, for corresponding application PCT/EP2010/052188, date of mailing May 28, 2010.
Bachstez et al., Über die Konstitiution der Orotsäure, Berichte Der Deutschen Chemischen Gesellschaft, vol. 63, Jun. 1, 1930, pp. 1000-1007.

*Primary Examiner* — Jeffrey Murray
(74) *Attorney, Agent, or Firm* — Michael P. Morris; Alan R. Stempel

(57) ABSTRACT

Subject of the present invention is a new improved process for the preparation of nitroorotic acid via nitration of orotic acid.

9 Claims, No Drawings

PROCESS FOR THE PREPARATION OF NITROOROTIC ACID

Subject of the present invention is a new process for the preparation of nitroorotic acid (II), which is obtained by nitration of orotic acid (I) according to the following reaction scheme:

Reaction Scheme 1

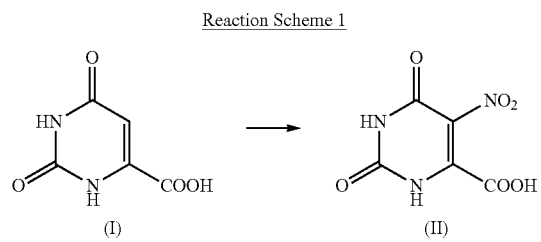

Nitroorotic acid is a key intermediate in the synthesis of dipyridamole, which is an active ingredient in Persantin® (sole active ingredient) and Aggrenox® (in combination with acetylsalicylic acid). Persantin® is a medicament used for preventing thrombosis and embolic events, Aggrenox® is a medicament used for the prevention of stroke.

Several other processes for preparing nitroorotic acid are known from the prior art.

A synthesis of the potassium salt of nitroorotic acid starting from orotic acid is described by M. Bachstez in Ber. dtsch. chem. Ges. 63 (1930) 1000. The synthesis was done only in a small laboratory scale, using a mixture of nitric and sulphuric acid as reagent. Most of the educt did either not react or decomposed, so that as a consequence, the yield of the product was very low.

In Ann. 456 (1924) 165, H. Biltz and E. Kramer decribe the preparation of nitroorotic acid in form of yellow needles decomposing at 236° C. by reacting orotic acid with fuming nitric acid, without giving any details about the reaction conditions or the yield.

F. G. Fischer and J. Roch (Ann. 572 (1951) 217) describe a laboratory scale process for preparing the potassium salt of nitroorotic acid using 4-methyl-2-thiouracil as starting material. They obtained the product in a yield of 50-55%.

Both R. Behrend and O. Roosen (Ann. 251 (1889) 238) and H. Biltz and M. Heyn (Ann. 413 (1916) 110) describe the synthesis of the potassium salt of nitroorotic acid starting from methyluracil in laboratory scale.

Presently, the nitroorotic acid needed for the manufacture of Persantin is produced by a large scale process based on nitration and oxidation of 6-methyluracil using fuming nitric acid. For the nitration step, the reaction temperature has to be maintained in a range of between 20° C. and 30° C. The oxidation step requires a temperature of up to 100° C.

Due to the high reaction temperature during the oxidation step, the whole reaction system may become instable, if the temperature is not controlled properly. The technical measurements, which are needed to regulate the system and to control the temperature in order to avoid e.g. decomposition, are highly expensive. The maximum yield of the current process is about 80% of the theory. A byproduct of this process is nitrogen dioxide, a toxic gas. For each mole of the starting material 6-methyluracil, 6 moles of nitrogen dioxide are set free, which have to be disposed of properly.

AIM OF THE INVENTION

The aim of the present invention is to overcome the problems linked to the present process for producing nitroorotic acid, to improve the known process for preparing nitroorotic acid, particularly with respect to both economic (yield, costs and availability of starting material) and ecologic (protection of the environment) aspects of a large scale process, and to enhance the safety (protection of employees) of the process.

SUBJECT OF THE INVENTION

Subject of the present invention is a new improved process for the preparation of nitroorotic acid via nitration of orotic acid according to reaction scheme 1.

Surprisingly, it has been found that the process according to the invention solves the problems related to the present synthetic route.

Most importantly, the development of toxic nitrous fumes such as nitrogen dioxide can completely be avoided by using the process according to the invention, because instead of fumed nitric acid as according to the prior art, 65% nitric acid is used. This reduces pollution as well as risks, and is an advantage with respect to safety and environment protection.

Furthermore, the educt is readily available in good quality and at a reasonable price, because it is widely used (several 100 tons per year) as an ingredient for animal food. The reagents are very common and inexpensive chemicals, too, so that the costs of goods are low.

Energy costs are reduced, since the reaction temperature is significantly lower than in the process known from the prior art. Furthermore, due to the lower reaction temperature particularly during the oxidation step, no expensive technical measurements for system regulation and temperature control are needed.

Both, the yield of the product (about 90%) and its purity are high resp. very high. This enhances the profitability of the process, and simultaneously reduces the efforts needed for purification.

Contrary to the known process, even at production scale, the process of invention does not require any special equipment for controlling the reaction due to safety issues.

Another advantage of the process according to the invention is that it can be conducted as a semi-batch process, i.e. that the educt (orotid acid) does not need to be added all at once, but may be added portionwise to the mixture of sulphuric and nitric acid. The next portion of orotic is added to the reaction mixture only after the previous portion was transformed into the product. This procedure, which was not possible according to the old method, helps to control the reaction in a simple, but effective way. Energy (and temperature) peaks can thus be avoided.

Additionally, after quenching the reaction mixture in water, the nitroorotic acid can be isolated as free acid, and thus, does not need to be set free from its salt prior to the next reaction step in the synthesis of dipyridamole, thereby avoiding additional working steps and saving time.

Furthermore, after quenching the reaction mixture in water, the water-containing product thus obtained may be used directly in the next step without that it is necessary to dry it previously, thereby saving time and costs. Due to the very high purity, the product of the subsequent step in the synthesis of dipyridamole does not need to be isolated.

Finally, the sulphuric acid used in the reaction can be recycled directly, after concentration. This is both reducing costs and protecting the environment.

DETAILED DESCRIPTION OF THE INVENTION

Nitroorotic acid (II) is produced by nitration of orotic acid (I) according to reaction scheme 1.

As the reagent, a mixture of concentrated sulphuric acid and concentrated (but not fuming) nitric acid is used. Preferably, the concentration of the sulphuric acid is 98% and the concentration of the nitric acid is 65%. Usually, sulphuric acid and nitric acid are mixed in a molar ratio of between 1:1 and 6:1. Preferably, the ratio of sulfuric acid to nitric acid is about 3:1 (in mole).

The nitration is carried out at a temperature of about 40-80° C. The preferred reaction temperature is about 40-60° C.; even more preferred is a reaction temperature of about 50-60° C.

No ethanol is added to the reaction mixture.

The nitroorotic acid such produced is susceptible to form hydrates.

Example

Nitroorotic Acid (Obtained Via Nitration of Orotic Acid)

With cooling below 50° C., 420 ml (7.68 mol) concentrated sulphuric acid ($H_2SO_4$, approx. 98%) were added to 169 ml (2.56 mol) 65% nitric acid ($HNO_3$). Then, 200 g orotic acid (1.28 mol; purity 99.64%) were added portionwise. The reaction mixture was heated to 50-55° C. under stirring for 3 hours.

After completion of the nitration, the reaction mixture was allowed to cool down to ambient temperature (about 10-15° C.), and was then poured into 800 ml of water under cooling below 30° C. While the resulting mixture was cooled to about 0-10° C., it was stirred slowly. The precipitated product was filtered off and washed with a small amount of cold water, and then dried at about 50-60° C.

Yield: 230 g (90%) based on waterfree material
Purity: 98.89% (HPLC)
Decomposition above 230° C.
MS (ESI): 202 ($MH^+$)
$^{13}C$-NMR (500 MHz, $D_2O$, ppm): 122.6, 150.1, 151.7, 158.3, 162.7

The invention claimed is:

1. A process for the preparation of nitroorotic acid wherein orotic acid is nitrated at a temperature of about 40-80° C. using a mixture of concentrated sulphuric acid and concentrated, but not fuming nitric acid.

2. The process according to claim 1 wherein the concentration of the nitric acid is about 65%.

3. The process according to claim 1 wherein the nitration is carried out at a temperature of about 40-60° C.

4. The process according to claim 3 wherein the nitration is carried out at a temperature of about 50-60° C.

5. The process according to claim 1 wherein the molar ratio between sulphuric acid and nitric acid is between 1:1 and 6:1.

6. The process according to claim 5 wherein the molar ratio between sulfuric acid and nitric acid is about 3:1.

7. The process according to claim 1 wherein orotic acid is added portionwise to the mixture of sulphuric acid and nitric acid.

8. The process according to claim 1 wherein the reaction mixture does not contain any ethanol.

9. The process according to claim 1 for large scale industrial production.

* * * * *